(12) United States Patent
Heinrich et al.

(10) Patent No.: US 9,775,616 B2
(45) Date of Patent: *Oct. 3, 2017

(54) METHODS AND APPARATUS FOR ANASTOMOSIS INCLUDING EXPANDABLE ANCHOR

(71) Applicant: COVIDIEN LP, Mansfield, MA (US)

(72) Inventors: Russell Heinrich, Madison, CT (US); Scott E. Manzo, Shelton, CT (US)

(73) Assignee: Covidien LP, Mansfield, MA (US)

( * ) Notice: Subject to any disclaimer, the term of this patent is extended or adjusted under 35 U.S.C. 154(b) by 604 days.

This patent is subject to a terminal disclaimer.

(21) Appl. No.: 14/231,974

(22) Filed: Apr. 1, 2014

(65) Prior Publication Data

US 2014/0214056 A1    Jul. 31, 2014

Related U.S. Application Data

(60) Continuation of application No. 12/638,549, filed on Dec. 15, 2009, now Pat. No. 8,715,304, which is a (Continued)

(51) Int. Cl.
*A61B 17/08* (2006.01)
*A61B 17/11* (2006.01)
*A61B 17/00* (2006.01)

(52) U.S. Cl.
CPC ..... *A61B 17/11* (2013.01); *A61B 2017/00557* (2013.01); *A61B 2017/00867* (2013.01); (Continued)

(58) Field of Classification Search
CPC ..... A61F 2/958; A61F 2/064; A61M 25/1011; A61M 25/1015; A61M 2025/1013; A61M 2025/1052; A61B 17/11; A61B 2017/1103; A61B 2017/1107; A61B 2017/00557; A61B 2017/1132; A61B 2017/1135; A61B 2017/1139; A61B 17/00491

See application file for complete search history.

(56) References Cited

U.S. PATENT DOCUMENTS 4,911,164 A   3/1990 Roth
5,002,557 A   3/1991 Hasson
(Continued)

FOREIGN PATENT DOCUMENTS

WO   WO 00/59380   10/2000
WO   WO 02/05719    1/2002
(Continued)

OTHER PUBLICATIONS

International Search Report corresponding to PCT/US03/11913, completed Dec. 4, 2003 and mailed Jan. 15, 2004; (4 pp).

*Primary Examiner* — Darwin Erezo
*Assistant Examiner* — Erin Colello

(57) ABSTRACT

The present disclosure is directed to devices for approximating body vessels and method for performing the same. In accordance with one aspect of the present disclosure, the device includes an inner member having a first expandable anchor operatively coupled near a distal end thereof, an outer member having a second expandable anchor, and a sleeve disposed about at least a portion of the inner member and the outer member.

16 Claims, 7 Drawing Sheets

Related U.S. Application Data division of application No. 10/503,743, filed as application No. PCT/US03/11913 on Apr. 16, 2003, now Pat. No. 7,648,515.

(60) Provisional application No. 60/373,223, filed on Apr. 16, 2002.

(52) U.S. Cl.
CPC ............... *A61B 2017/1107* (2013.01); *A61B 2017/1135* (2013.01)

(56) References Cited

U.S. PATENT DOCUMENTS

| | | | |
|---|---|---|---|
| 5,047,039 A | 9/1991 | Avant et al. | |
| 5,146,925 A * | 9/1992 | Snow | A61M 25/04 600/435 |
| 5,176,697 A | 1/1993 | Hasson et al. | |
| 5,290,249 A | 3/1994 | Foster et al. | |
| 5,312,343 A * | 5/1994 | Krog | A61M 25/1011 604/101.03 |
| 5,385,606 A | 1/1995 | Kowanko | |
| 5,395,311 A | 3/1995 | Andrews | |
| 5,419,763 A | 5/1995 | Hildebrand | |
| 5,445,615 A | 8/1995 | Yoon | |
| 5,464,415 A | 11/1995 | Chen | |
| 5,484,412 A | 1/1996 | Pierpont | |
| 5,540,701 A * | 7/1996 | Sharkey | A61B 17/11 606/153 |
| 5,545,171 A | 8/1996 | Sharkey et al. | |
| 5,549,122 A | 8/1996 | Detweilwer | |
| 5,591,179 A | 1/1997 | Edelstein | |
| 5,599,307 A | 2/1997 | Bacher et al. | |
| 5,634,936 A * | 6/1997 | Linden | A61B 17/0057 604/60 |
| 5,697,946 A * | 12/1997 | Hopper | A61B 17/3421 606/185 |
| 5,749,890 A * | 5/1998 | Shaknovich | A61F 2/958 128/898 |
| 5,807,398 A * | 9/1998 | Shaknovich | A61F 2/01 606/194 |
| 5,873,889 A | 2/1999 | Chin | |
| 5,968,065 A | 10/1999 | Chin | |
| 5,971,954 A | 10/1999 | Conway et al. | |
| 5,976,168 A | 11/1999 | Chin | |
| 5,980,549 A | 11/1999 | Chin | |
| 6,007,613 A | 12/1999 | Izoret | |
| 6,022,336 A | 2/2000 | Zadno-Azizi et al. | |
| 6,026,814 A * | 2/2000 | LaFontaine | A61F 2/06 128/898 |
| 6,068,637 A | 5/2000 | Popov et al. | |
| 6,165,196 A | 12/2000 | Stack et al. | |
| 6,176,864 B1 | 1/2001 | Chapman | |
| 6,203,557 B1 | 3/2001 | Chin | |
| 6,241,741 B1 | 6/2001 | Duhaylongsod et al. | |
| 6,245,083 B1 * | 6/2001 | Black | A61B 17/11 606/153 |
| 6,248,117 B1 | 6/2001 | Blatter | |
| 6,277,137 B1 | 8/2001 | Chin | |
| 6,390,098 B1 | 5/2002 | LaFontaine et al. | |
| 6,409,723 B1 | 6/2002 | Edwards | |
| 6,450,989 B2 * | 9/2002 | Dubrul | A61F 2/958 604/104 |
| 6,471,672 B1 * | 10/2002 | Brown | A61F 2/958 604/101.01 |
| 6,485,500 B1 * | 11/2002 | Kokish | A61M 25/104 604/101.01 |
| 6,524,283 B1 | 2/2003 | Hopper et al. | |
| 6,602,263 B1 * | 8/2003 | Swanson | A61B 17/11 606/139 |
| 6,616,675 B1 * | 9/2003 | Evard | A61B 1/3137 606/153 |
| 6,626,939 B1 | 9/2003 | Burnside et al. | |
| 6,716,252 B2 | 4/2004 | Lazarovitz et al. | |
| 6,773,452 B2 | 8/2004 | Shaker | |
| 6,911,038 B2 * | 6/2005 | Mertens | A61F 2/958 606/192 |
| 7,105,002 B2 | 9/2006 | Chapman | |
| 7,648,515 B2 | 1/2010 | Heinrich et al. | |
| 2001/0007069 A1 * | 7/2001 | Bombard | A61B 17/064 606/41 |
| 2001/0020189 A1 | 9/2001 | Taylor | |
| 2001/0039426 A1 * | 11/2001 | Makower | A61B 17/0401 606/153 |
| 2002/0091398 A1 | 7/2002 | Galdonik et al. | |
| 2003/0135227 A1 | 7/2003 | Chapman | |
| 2003/0229364 A1 | 12/2003 | Seiba | |
| 2004/0024355 A1 | 2/2004 | Tsukada | |
| 2004/0087995 A1 * | 5/2004 | Copa | A61B 17/11 606/192 |
| 2005/0070938 A1 | 3/2005 | Copa et al. | |
| 2005/0131431 A1 | 6/2005 | Copa et al. | |
| 2005/0165378 A1 | 7/2005 | Heinrich et al. | |
| 2005/0165432 A1 | 7/2005 | Heinrich | |
| 2005/0171563 A1 | 8/2005 | Heinrich et al. | |
| 2005/0171564 A1 | 8/2005 | Manzo | |
| 2005/0240205 A1 * | 10/2005 | Berg | A61B 17/064 606/153 |
| 2006/0206189 A1 | 9/2006 | Furst et al. | |

FOREIGN PATENT DOCUMENTS

| | | |
|---|---|---|
| WO | WO 03/088847 | 10/2003 |
| WO | WO 03/094994 | 11/2003 |
| WO | WO 04/000093 | 12/2003 |
| WO | WO 04/000134 | 12/2003 |
| WO | WO 04/000135 | 12/2003 |
| WO | WO 04/000136 | 12/2003 |
| WO | WO 2004/098417 | 11/2004 |

* cited by examiner

METHODS AND APPARATUS FOR ANASTOMOSIS INCLUDING EXPANDABLE ANCHOR

CROSS-REFERENCE TO RELATED APPLICATION

The present application is a Continuation Application claiming the benefit of and priority to U.S. patent application Ser. No. 12/638,549, filed Dec. 15, 2009, which is a Divisional Application claiming the benefit of and priority to U.S. patent application Ser. No. 10/503,743, filed on Aug. 4, 2004 (now U.S. Pat. No. 7,648,515), which is a National Phase Application filed under 35 U.S.C. §371 of International Application Serial No. PCT/US2003/011913, filed on Apr. 16, 2003, which claims the benefit of and priority to U.S. Provisional Application Ser. No. 60/373,223 filed on Apr. 16, 2002, the entire contents of which are incorporated herein by reference.

BACKGROUND

1. Technical Field

The present disclosure relates to devices and methods used for joining tissue portions and, more particularly, to anastomotic devices and methods for positioning and joining tissue cavities to one another. The present disclosure also relates to devices with anchors and methods of using the same.

2. Background of Related Art

Anastomosis is the joining of two hollow or tubular structures. For example, the removal of cancerous growth or treatment of cancerous tissue can result in a need to connect two portions of organs or two body conduits in fluid communication with one another. Most body conduits are generally cylindrical in configuration and have a generally circular cross-section. When it is desired to suture such a conduit to another body conduit, typically sutures are placed around the circumference of the conduits in order to maintain their patency and in order to maintain its lumen or channel. It can be appreciated that the sutures made on top of the conduits in at least certain anastomotic procedures are made relatively easier than the sutures made underneath the conduits.

The complexity of anastomosis attachment is made manifestly apparent in a surgical procedure referred to generally as a radical prostatectomy (i.e., a well established surgical procedure for patients with localized prostatic carcinoma). Radical prostatectomy procedures, for example, require the removal of the cancerous tissue while attempting to preserve the sexual capability and continence of a patient.

The radical prostatectomy surgical procedure is generally concluded with the joining of the bladder, in particular the bladder neck, to the urethra, in particular the urethral stump, preparing and positioning the bladder and urethra for a mucosa-to-mucosa joining, and suturing the bladder neck and the urethral stump in position. This may be accomplished using minimally invasive surgery. The current radical prostatectomy procedure is hampered by poor accessibility, the friable nature of the urethra, and the close proximity of important sexual and continence related organs to the surgical site. In addition, the radical prostatectomy procedure is further complicated by the tendency of the urethral stump to retract into adjacent tissue. As a result, considerable time and effort must be expended to re-expose the urethral stump and begin the anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating a radical prostatectomy procedure. In U.S. Pat. No. 5,591,179 issued to Edelstein there is disclosed a suturing device including a shaft with portions defining an interior channel extending between the proximal and distal ends of the shaft. This channel includes a generally axial lumen which extends to the proximal end and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164 issued to Roth there is disclosed a suture guide with a curved distal portion. This distal portion has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039 issued to Avant et al. there is disclosed a surgical device for the ligation of a dorsal vein and subsequent anastomosis. This device contains a pair of enclosed needles each having an attached suture which needles may be driven from the shaft of the device into adjacent tissue.

In addition, surgical anastomosis instruments having a "one shot" approach for quickly securing two vessel portions have been developed and include end-to-side anastomosis instruments which are typically used in the aortic and coronary regions of the body. End-to-end and side-to-side anastomosis instruments for joining vessel portions together are also well known. These instruments typically use metal fasteners or staples having a "U" or a "C" shape to join the tissue portions to one another. There are applications, however, such as with the urethra, where the use of metal fasteners or staples are known to increase the likelihood of future complications.

Accordingly, a continuing need exists for anastomosis devices for performing procedures such as a radical prostatectomy that can position one vessel portion, e.g., the bladder and/or bladder neck, adjacent a second vessel portion, e.g., the urethra and/or urethral stump, for anastomosis without the use of minimally invasive surgery or the use of sutures, clips and/or staples. In addition, a continuing need exists for anastomosis devices which reduce the amount of handling of the vessel portions which can ultimately lead to poor recovery of a vessel function.

SUMMARY

The present disclosure is directed to devices for approximating body vessels. According to an aspect of the present disclosure, a device for approximating body vessels includes an inner member having a first expandable anchor operatively coupled near a distal end thereof, an outer member having a lumen and disposed about the inner member, the outer member having a second expandable anchor, and a radially expandable sleeve disposed about at least a portion of the outer member for engaging the juncture of portions of the body vessels. It is desirable that the inner member has a lumen.

It is envisioned that the first expandable anchor and the second expandable anchor are configured and adapted to radially expand the sleeve. The first expandable anchor has an initial condition in which the radius of the expandable anchor is substantially equal to the radius of the inner member and an expanded condition in which the radius of the expandable anchor is larger than the radius of the inner member. The second expandable anchor has an initial condition in which the radius of the second expandable anchor is substantially equal to the radius of the outer member and an expanded condition in which the radius of the second expandable anchor is larger than the radius of the outer member.

It is envisioned that the device further includes a third expandable anchor on the outer member, the first, second and third expandable anchors being separately expandable.

The sleeve is preferably made from a porous material. More preferably, the sleeve is made of substantially non-elastic filaments. It is envisioned that the sleeve is made from a braid of filaments arranged so that radial expansion of the sleeve result in axial shortening of the braid. It is further envisioned that the sleeve is made from a bio-absorbable material. The bio-absorbable material is at least one of polyglycolic acid and polylactic acid. The sleeve is desirably impregnated with a medical adhesive.

It is envisioned that at least one of the first expandable anchor, and the second expandable anchor is expandable via fluid inflation. It is further envisioned that at least one of the first expandable anchor and the second expandable anchor comprises a balloon.

The inner member includes an inflation/deflation lumen extending therethrough, and wherein the inflation/deflation lumen of the inner member is in fluid communication with the first expandable anchor. The outer member includes an inflation/deflation lumen for the second expandable anchor in fluid communication with the second expandable anchor.

The first expandable anchor is made of an expandable and/or stretchable material having suitable structural integrity and strength for the movement, positioning and/or repositioning of at least a portion of a body organ.

According to another aspect of the present disclosure, the device for performing a surgical anastomosis includes an inner catheter having a distal end, a proximal end and defining an axial lumen therethrough, the inner catheter including a first expandable anchor operatively coupled near the distal end thereof, an outer catheter having a distal end, a proximal end and a lumen for receiving the inner catheter extending therethrough, and a radially expandable sleeve disposed about at least a portion of the inner catheter and at least a portion of the outer catheter for engaging the juncture between portions of two body vessels. The outer catheter includes a distal expandable anchor operatively coupled near the distal end of the outer catheter, and a proximal expandable anchor operatively coupled near the distal end of the outer catheter at a location proximal of the distal expandable anchor.

It is envisioned that at least one of the expandable anchor, the distal expandable anchor and the proximal expandable anchor is expandable by fluid inflation. It is further envisioned that at least one of the expandable anchor, the distal expandable anchor and the proximal expandable anchor comprises a balloon.

The inner catheter includes an inflation/deflation lumen extending therethrough, wherein the inflation/deflation lumen of the inner catheter is in fluid communication with the first expandable anchor. The outer catheter includes an inflation/deflation lumen for each of the distal expandable anchor and the proximal expandable anchor extending therethrough, wherein each inflation/deflation lumen is in fluid communication with a respective distal expandable anchor and proximal expandable anchor.

The sleeve is made from a braid of individual substantially non-elastic filaments so that radial expansion of the sleeve results in axial shortening of the sleeve. Preferably, the sleeve is made from a porous material. It is contemplated that the sleeve is impregnated with a medical adhesive.

The sleeve has a first condition having a first radius which is substantially equal to a radius of the outer catheter and a second condition having a second radius which is larger than the radius of the outer catheter.

According to another aspect of the present disclosure, a method of approximating a first body vessel and a second body vessel is provided. The method includes the step of providing a device for performing the surgical anastomosis. The device includes an inner member having a first expandable anchor operatively coupled near a distal end thereof, an outer member having a lumen for receiving the inner member, the outer member having a second expandable anchor, and a radially expandable sleeve disposed about at least a portion of the outer member for engaging the juncture of the body vessels.

The method further includes the steps of passing the device through the first body vessel and into the second body vessel, engaging the first expandable anchor with the second body vessel such that the distal end of the sleeve engages the second body vessel, engaging the second expandable anchor of the outer member with the first body vessel, moving the inner member so that the second body vessel contacts the first body vessel, and engaging the second expandable anchor with the first body vessel such that a proximal end of the sleeve engages the first body vessel.

It is envisioned that the steps of engaging includes expanding at least one of the first and second expandable anchors.

It is envisioned that the method further includes the step of retracting the first expandable anchor and the second expandable anchor in order to withdraw the device from the first and second body vessels. It is further envisioned that the method further includes the step of applying a medical adhesive between the sleeve and both of the first body vessel and the second body vessel.

The sleeve includes a porous material. It is envisioned that the method further includes impregnating the sleeve with a medical adhesive. The sleeve is made from a braid of individual non-elastic filaments so that radial expansion of the sleeve results in axial shortening of the sleeve.

It is envisioned that at least one of the first expandable anchor and the second expandable anchor are expandable via inflation. The method further includes the step of inflating the at least one of the first expandable anchor and the second expandable anchor.

According to a further aspect of the disclosure, a device for performing a surgical anastomosis is disclosed. The device includes an inner member having a first expandable anchor operatively coupled near a distal end thereof, wherein the first expandable anchor includes a proximal end portion defining an annular concave region when in an expanded condition, the annular concave region of the expandable anchor being configured and adapted to evert a portion of body tissue when the expandable anchor is expanded, and an outer member having a lumen for receiving the inner member.

It is envisioned that the device further includes a second expandable anchor operatively coupled to the outer member. The first expandable anchor has a retracted condition in which the radius of the first expandable anchor is substantially equal to the radius of the inner member and an expanded condition in which the radius of the first expandable anchor is larger than the radius of the inner member. The second expandable anchor has a retracted condition in which the radius of the second expandable anchor is substantially equal to the radius of the outer member and an expanded condition in which the radius of the second expandable anchor is larger than the radius of the outer member. It is envisioned that the device further includes a proximal expandable anchor with a retracted condition in which the radius of the proximal expandable anchor is substantially equal to the radius of the outer member and an expanded condition in which the radius of the proximal expandable anchor is larger than the radius of the outer member.

The first expandable anchor is expandable via fluid inflation. It is envisioned that the first expandable anchor is made of an expandable and/or stretchable material having suitable structural integrity and strength for the movement, positioning and/or repositioning of at least a portion of a body organ. The first expandable anchor includes a balloon.

It is envisioned that the outer member is slidably disposed about the inner member, the outer member having a distal expandable anchor operatively coupled near a distal end of the outer member, wherein the distal expandable anchor includes a distal portion defining an annular concave region when in an expanded condition, the annular concave region of the distal expandable anchor being configured and adapted to evert a portion of body tissue when the distal expandable anchor is expanded.

According to a further aspect of the present disclosure, a method of approximating a first body vessel and a second body vessel is provided. The method includes the steps of providing a member having a distal end and an expandable anchor disposed at the distal end, the expandable anchor comprising a membrane defining a chamber, introducing the member through the first body vessel and into the second body vessel, expanding the expandable anchor by introducing a fluid into the chamber, so that the expandable anchor engages the second body vessel, and moving the second body vessel toward the first body vessel.

The method further includes deploying fastening means connecting the first body vessel and the second body vessel. The method still further includes collapsing the expandable anchor and removing the member and the expandable anchor.

It is envisioned that the member includes an inner member and further comprising an outer member having a lumen for receiving the inner member, the outer member having an expandable anchor. The method further includes expanding the expandable anchor after the step of moving the second body vessel, so that the expandable anchor engages the first body vessel.

According to yet another aspect of the present disclosure, a device for approximating body vessels is provided. The device includes a member having a distal end and an expandable anchor disposed at the distal end, the expandable anchor comprising a membrane defining a chamber, and fastening means carried by the expandable anchor for engaging the body vessels.

The fastening means includes a sleeve disposed around the expandable anchor so that upon expansion of the expandable anchor, the sleeve engages the body vessel. The fastening means includes a medical adhesive. The member includes an inner member and further includes an outer member having a lumen for receiving the inner member and expandable anchor thereon. Preferably, the outer member is movable with respect to the inner member for positioning the fastening means. It is envisioned that the device further includes an expandable cuff on the outer member.

These objects together with other objects of the disclosure, along with the various features of novelty which characterize the disclosure, are pointed out with particularity in the claims annexed to and forming a part of this disclosure.

BRIEF DESCRIPTION OF THE DRAWINGS

By way of example only, preferred embodiments of the present disclosure will be described herein with reference to the accompanying drawings, in which.

DETAILED DESCRIPTION OF PREFERRED EMBODIMENTS

Figure 1:
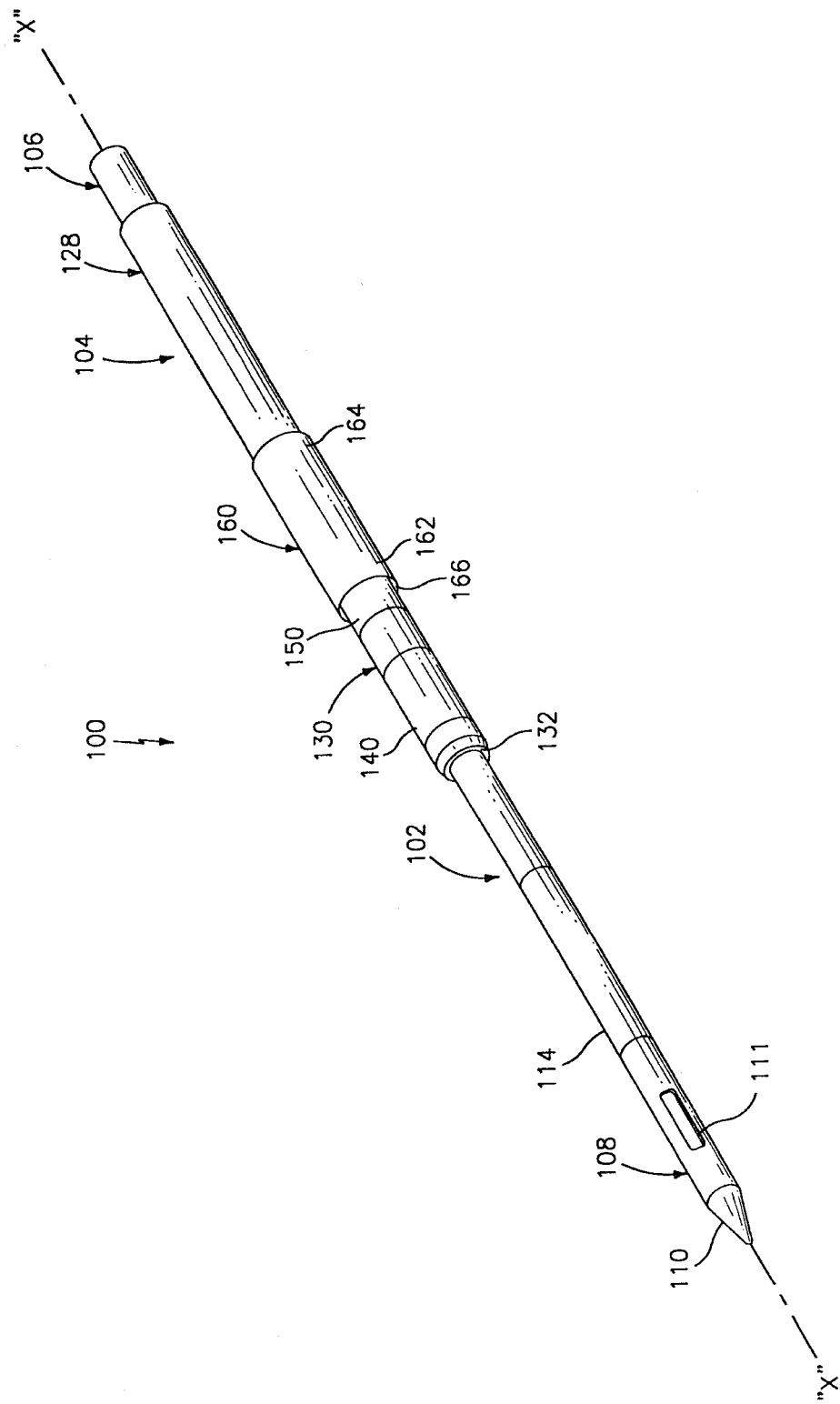
FIG. 1 is a perspective view of a device for performing a surgical procedure, in accordance with an embodiment of the present disclosure, shown in an insertion and/or a withdrawal condition.

Preferred embodiments of the presently disclosed surgical device will now be described in detail with reference to the drawing figures wherein like reference numerals identify similar or identical elements. In the drawings and in the description which follows, the term "proximal", as is traditional will refer to the end of the surgical applier which is closest to the operator, while the term "distal" will refer to the end of the applier which is furthest from the operator.

Referring to FIGS. 1-9, embodiments of devices for performing anastomotic procedures, in accordance with the principles of the present disclosure, are shown generally as reference numeral 100. Although device 100 offers significant advantages to a radical prostatectomy procedure, it will be understood that the device is applicable for use in any anastomotic procedure where at least two body vessels are to be joined, such as joining the end of a conduit to a hollow body organ.

Figure 2:
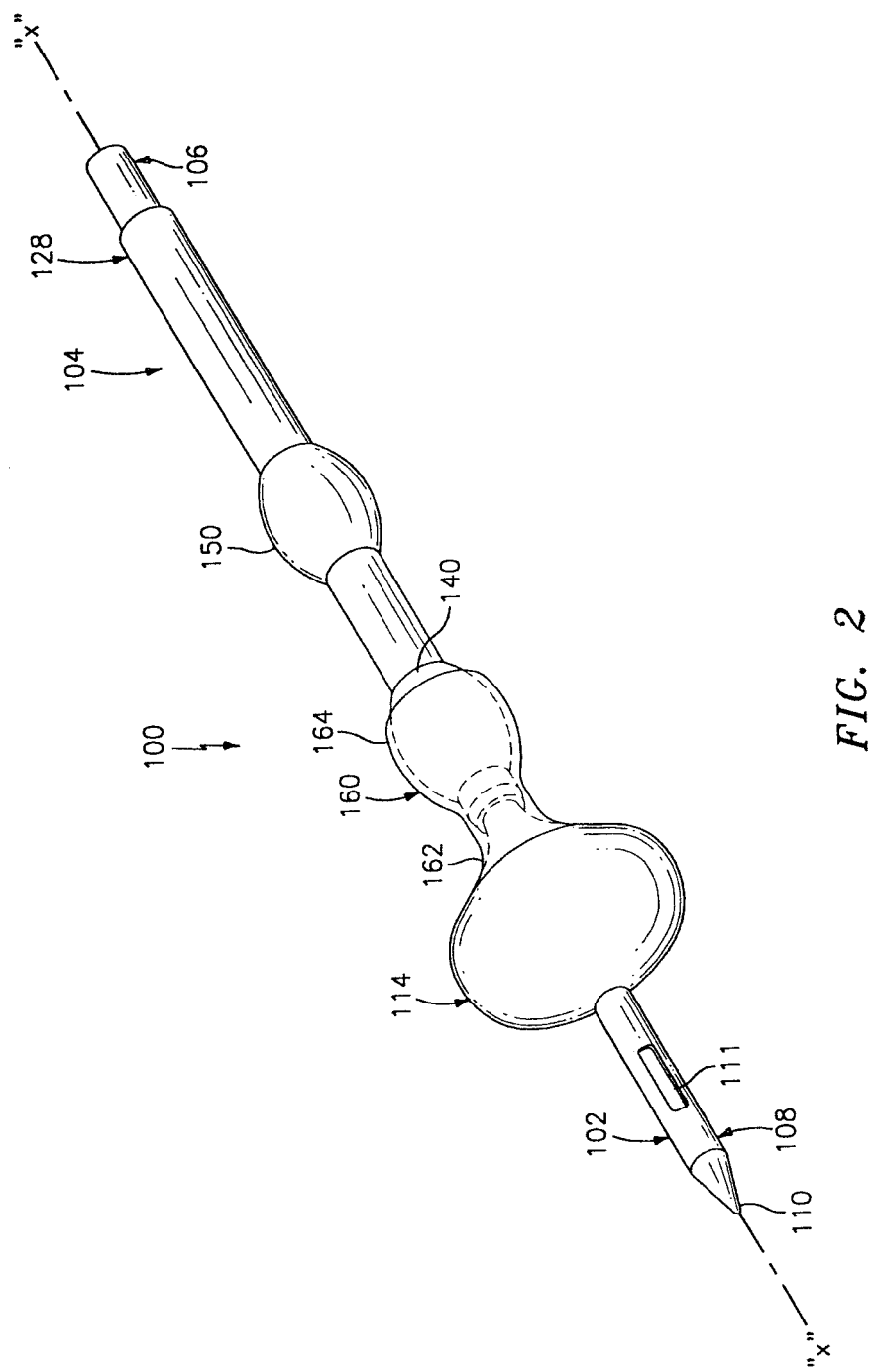
FIG. 2 is a perspective view of the device in accordance with the embodiment of FIG. 1, shown in an anchoring and anastomosis condition.

Referring now in specific detail to the drawings in which like reference numerals identify similar or identical elements throughout the several views, and initially to FIGS. 1 and 2, anastomotic device 100 is shown in a first condition (i.e., insertion and/or withdrawal condition). The device is desirably configured for passage through a body lumen. Anastomotic device 100 includes a pair of concentric tubular members, preferably, an inner tubular member 102 and an outer tubular member 104 slidably disposed about inner tubular member 102. Inner tubular member 102 includes a proximal end 106 and a distal end 108. Preferably, distal end 108 is provided with a conical cap 110 in order to facilitate insertion of device 100 through the body lumen.

Inner tubular member 102 further includes an expandable anchor 114 provided near distal end 108 and proximal of an opening 111 formed near distal end 108 of inner tubular member 102. Preferably, expandable anchor 114 is configured and adapted to surround inner tubular member 102. Expandable anchor 114 has an initial condition, as seen in FIG. 1, in which expandable anchor 114 has a radius which is substantially equal to or less than a radius of inner tubular member 102 and an expanded condition, as seen in FIG. 2, in which expandable anchor 114 has a radius which is greater than the radius of the expandable anchor 114 in the initial condition. Accordingly, when expandable anchor 114 is in the initial condition, axial displacement of inner tubular member 102 through the body lumen is possible, and when expandable anchor 114 is in the expanded condition, axial movement of inner tubular member 102 through the body lumen is either restricted or prevented.

In the embodiment shown, expandable anchor 114 of inner tubular member 102 is a balloon-type anchor. Expandable anchor 114 includes a medical grade material and is desirably made of an expandable and/or stretchable material. The material of expandable anchor 114 has suitable structural integrity and reinforcement for the movement, positioning and/or repositioning of at least a portion of a hollow body organ after expandable anchor 114 has been inflated to the expanded condition. It is contemplated that the expandable anchor 114 may be reinforced using extra layers of material strategically positioned. The reinforcing material is desirably expandable and/or stretchable and may take the form of reinforcing strips attached at certain intervals along the surface of expandable anchor 114 to create a preferred structural shape.

Figure 8:
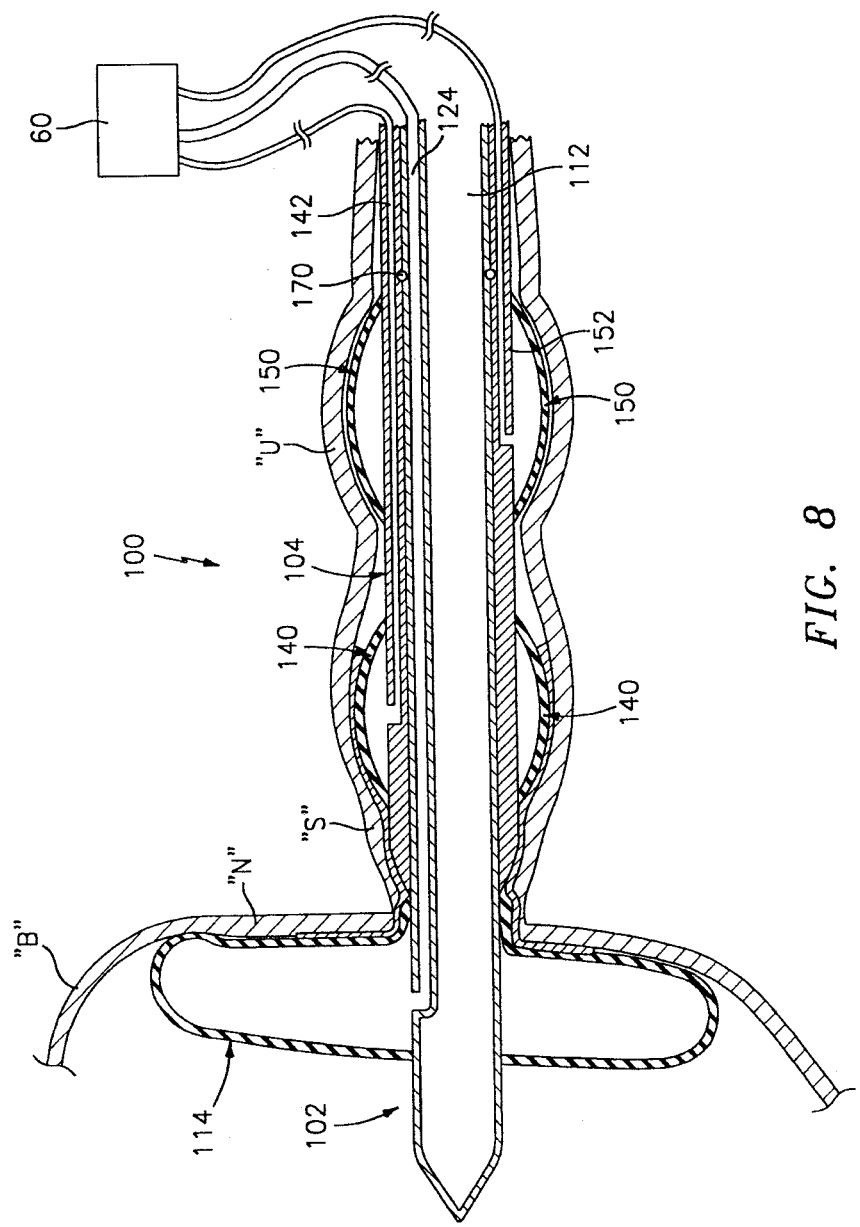
FIG. 8 is a cross-sectional side elevational view of a portion of the urinary system, taken along the longitudinal axis of a device of FIG. 1, illustrating the bladder approximated to the urethra and a device in accordance with the embodiment of FIGS. 1-7 in the anastomosis condition therewithin.

In a preferred embodiment, as seen in FIG. 8, inner tubular member 102 is provided with an inflation/deflation lumen 124 extending along the wall of central lumen 112 and is in fluid communication at a distal end thereof with expandable anchor 114 and at a proximal end thereof with a source of fluid 60 for inflation and/or deflation of expandable anchor 114. The fluid may include any liquid or gas that is safe for surgical applications. For example, air, carbon dioxide, or saline may be used.

Optionally, inner tubular member 102 includes at least one opening 111 formed near distal end 108 which opening 111 provides access to a central lumen 112 (see FIG. 8). Central lumen 112 of inner tubular member 102 defines a central longitudinal axis "X". If needed, opening 111 and central lumen 112 function much like a Foley-type catheter and permit fluid to be drained from or infused into the target operative site and/or define an access channel through which instruments can be passed, such as optical instruments, in order to aid in the viewing of surrounding tissue. Such access channels may also receive instruments other than optical instruments.

Returning to FIGS. 1 and 2, outer tubular member 104 includes a proximal end 128 and a distal end 130 defining a lumen 132 extending therethrough, in which inner tubular member 102 is slidably disposed. Outer tubular member 104 includes a distal expandable cuff or anchor 140 provided near distal end 130 thereof and a proximal expandable cuff or anchor 150 provided at a location proximal of distal expandable cuff 140. Each expandable cuff 140, 150 has an initial condition, as seen in FIG. 1, in which expandable cuff 140 or 150 has a radius which is substantially equal to a radius of outer tubular member 104 and an expanded condition, as seen in FIG. 2, in which expandable cuff 140 or 150 has a radius which is greater than the radius of outer tubular member 104.

In a preferred embodiment, as seen in FIG. 8, outer tubular member 104 is provided with a first inflation/deflation lumen 142 extending along the length thereof and which is in fluid communication at a distal end thereof with distal expandable cuff 140 and at a proximal end thereof with fluid source 60. Outer tubular member 104 is further provided with a second inflation/deflation lumen 152 extending along the length thereof and which is in fluid communication at a distal end thereof with proximal expandable cuff 150 and at a proximal end thereof with fluid source 60.

The expandable cuffs 140 and 150 desirably include balloon-type expandable cuffs. The balloon-type cuffs are made from material with suitable structural integrity and reinforcement for the movement, positioning and/or repositioning of at least a portion of a body vessel after expandable cuff 140 and/or 150 has been inflated to the expanded condition. The cuffs are made from medical grade material and may comprise expandable and/or stretchable material. Preferably, the outer surface of each expandable cuff 140 and 150 is configured to provide sufficient frictional contact with the inner surface of the body vessel when expandable cuff 140 and/or 150 is inflated.

Figure 6:
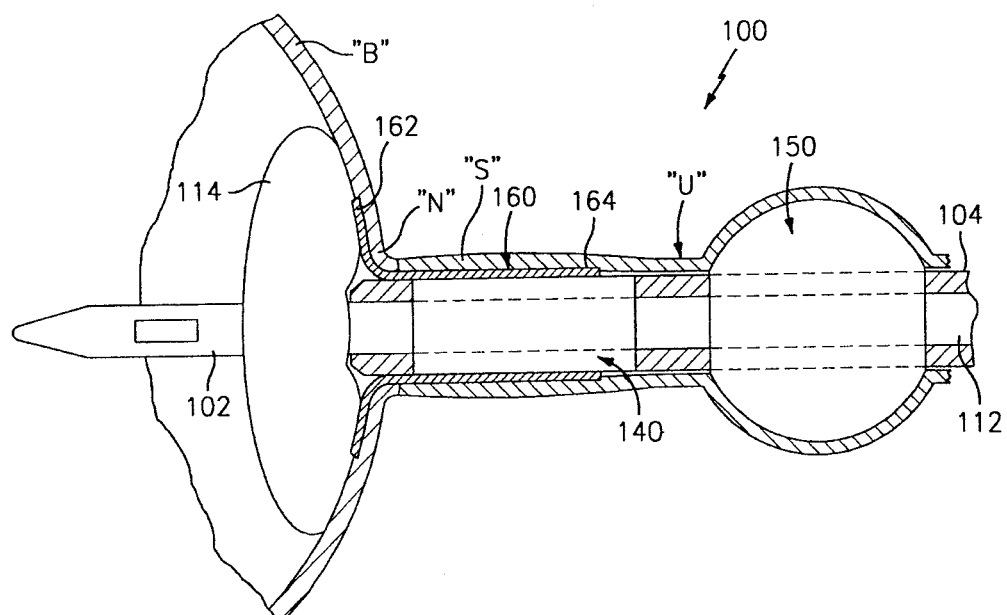
FIG. 6 is a partial cross-sectional side elevational view of a portion of the urinary system illustrating the bladder approximated to the urethra and a device in accordance with the embodiment of FIGS. 1-5 in the approximated condition therewithin.

Turning back to FIGS. 1 and 2, device 100 further includes a sleeve 160 slidably disposed about outer tubular member 104. Sleeve 160 includes a distal end 162, a proximal end 164 and defines a lumen 166 therethrough. Sleeve 160 preferably has a length sufficient to extend at least partially over both expandable anchor 114 of inner tubular member 102 and distal expandable cuff 140 of outer tubular member 104 when expandable anchor 114 and distal expandable cuff 140 are in their closest proximity to one another, such as, for example, when device 100 is in the approximated condition, as seen in FIG. 6.

Sleeve 160 is preferably made from a braid, mesh or any other deformable material suitable for radial expansion between a first condition having a first diameter and a second condition having a second diameter larger than the first diameter. More preferably, sleeve 160 is formed as a mesh of individual non-elastic filaments so that radial expansion of sleeve 160 results in axial shortening of sleeve 160. Such an axial shortening of sleeve 160 helps to maintain in an approximated condition, and/or further helps to approximate, the body vessels. Sleeve 160 may be of conventional construction, including round filaments, flat or ribbon filaments, square filaments, or the like. Non-round filaments may advantageously reduce the axial force required to provide radial expansion of sleeve 160.

Alternatively, it is envisioned that sleeve 160 can be a solid flexible, elastic or other deformable material, wherein an outer surface of sleeve 160 includes ridges, barbs, knurling or other high friction elements in order to assist in the engaging and retaining of the body vessels in apposition with one another.

As seen in FIG. 8, device 100 preferably further includes at least one annular seal (e.g. an O-ring) 170 disposed between inner tubular member 102 and outer tubular member 104. Accordingly, it is envisioned that annular seal 170 prevents or reduces the possibility of fluids from passing between inner tubular member 102 and outer tubular member 104.

Preferably, device 100 further includes a locking mechanism (not shown) for securing the position of inner tubular member 102 relative to outer tubular member 104 and to prevent their relative axial movement with respect to one another.

A preferred method of use and operation of anastomosis device 100, in a radical prostatectomy procedure, will now be described in greater detail with reference to FIGS. 1-9 and in particular with reference to FIGS. 3-9. With the prostrate removed, bladder neck "N" of bladder "B" is first reconstructed by everting the inner mucosal lining of bladder "B" and suturing the inner mucosal lining down to the outer wall of bladder "B" using known surgical techniques. Likewise, urethral stump "S" of urethra "U" is reconstructed by everting the inner mucosal lining of urethral stump "S" and suturing the inner mucosal lining down to the outer wall of urethra "U", using known surgical techniques.

Preferably, with bladder neck "N" reconstructed, bladder neck "N" is sized to properly accommodate and retain distal end 108 of inner tubular member 102 within bladder "B" using a standard tennis racket type closure (i.e., the opening of the bladder neck constituting the head of the tennis racket and a radial incision extending from the bladder neck constituting the handle portion of the tennis racket). Most preferably, bladder neck "N" is sized to be approximately 7-8 mm in diameter.

Figure 3:
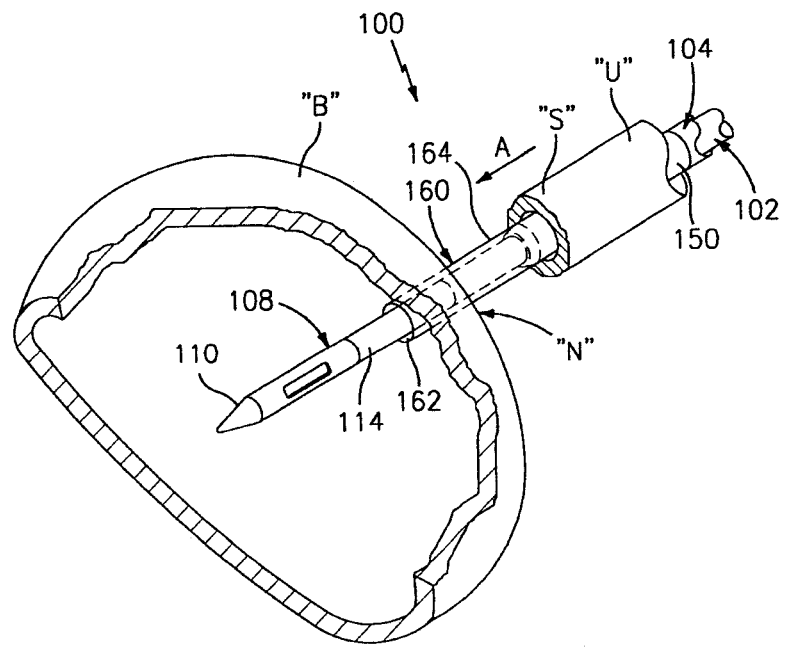
FIG. 3 is an enlarged perspective view of a distal end of a device in accordance with the embodiment of FIGS. 1-2, shown in the insertion or withdrawal condition, within a portion of a urinary system.

As seen in FIG. 3, with bladder neck "N" reconstructed, device 100, including inner tubular member 102, outer tubular member 104 and sleeve 160, is passed trans-urethrally through urethra "U" until distal end 108 of inner catheter 102 extends out of urethral stump "S" and into bladder "B" through bladder neck "N" as indicated by arrow "A". In particular, distal end 108 of inner tubular member 102 is preferably positioned such that expandable anchor 114 of inner tubular member 102 is positioned entirely within bladder "B". The device desirably includes a securement device, such as a sleeve 160. The sleeve 160 is preferably positioned along the length of inner tubular member 102 such that distal end 162 of sleeve 160 is disposed within bladder "B" and at least partially over and surrounding expandable anchor 114 of inner tubular member 102, and proximal end 164 of sleeve 160 extends proximally from bladder neck "N".

Figure 4:
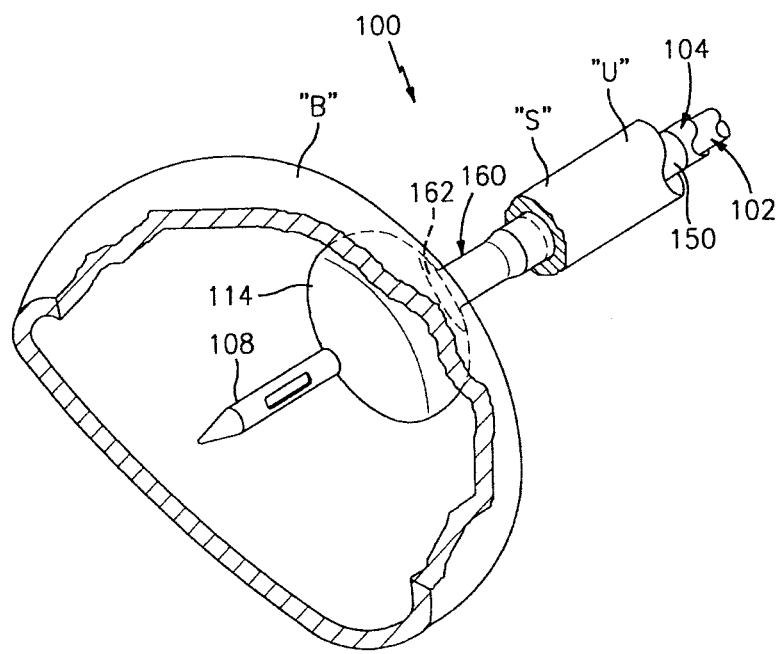
FIG. 4 is an enlarged perspective view of the distal end of a device in accordance with the embodiment of FIGS. 1-3, shown in a bladder anchoring condition, within a portion of a urinary system.

With expandable anchor 114 of inner tubular member 102 positioned at least substantially within bladder "B", as seen in FIG. 4, a fluid (e.g., air, carbon dioxide, saline or the like) is introduced through lumen 124 (FIG. 8) and into expandable anchor 114 in order to expand and inflate expandable anchor 114 within bladder "B". A syringe or similar means may be used to introduce the fluid. Inflation and expansion of expandable anchor 114 will inhibit withdrawal or prevent withdrawal of inner tubular member 102 from bladder "B", as well as causes distal end 162 of sleeve 160 to radially expand within bladder "B".

Figure 5:
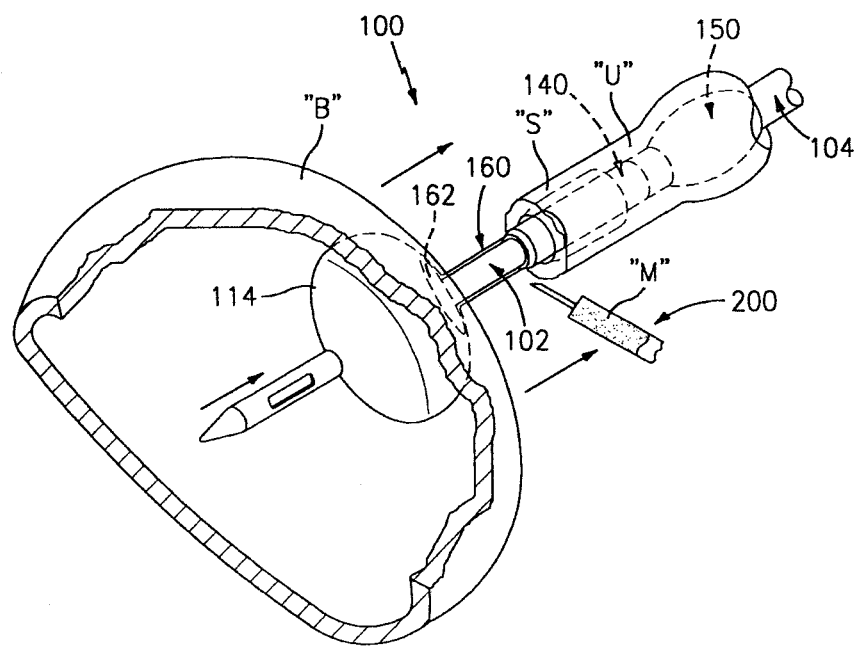
FIG. 5 is an enlarged perspective view of the distal end of a device in accordance with the embodiment of FIGS. 1-4, shown in a retracting and/or approximating condition, illustrating the approximation of the bladder to the urethra.

As seen in FIG. 5, outer tubular member 104 is desirably positioned within urethra "U" such that another anchoring device is positioned in close proximity with urethral stump "S". For example, in the embodiment shown, distal expandable cuff 140 is positioned in close proximity with urethral stump "S". With distal expandable cuff 140 positioned near urethral stump "S", a fluid (e.g., air, carbon dioxide, saline or the like) is introduced through inflation/deflation lumen 152 (FIG. 8) into proximal expandable cuff 150 to thereby expand and inflate proximal expandable cuff 150. Inflation and expansion of proximal expandable cuff 150 results in the radial expansion of proximal expandable cuff 150 and in turn the pressing of proximal expandable cuff 150 against the inner surface of urethra "U" (see FIGS. 5-8), thus preventing axial displacement of outer tubular member 104 relative to urethra "U".

With both expandable anchor 114 and proximal expandable cuff 150 in an expanded condition, as seen in FIG. 5, inner tubular member 102 is withdrawn through outer tubular member 104. As inner tubular member 102 is withdrawn through outer tubular member 104, in direction "D", bladder "B" is also moved in direction "D" and approximated toward urethral stump "S". It is contemplated that once bladder "B" has been approximated toward urethral stump "S", inner tubular member 102 can be locked in position relative to outer tubular member 104 thereby maintaining bladder "B" in approximation with urethra "U".

Figure 7:
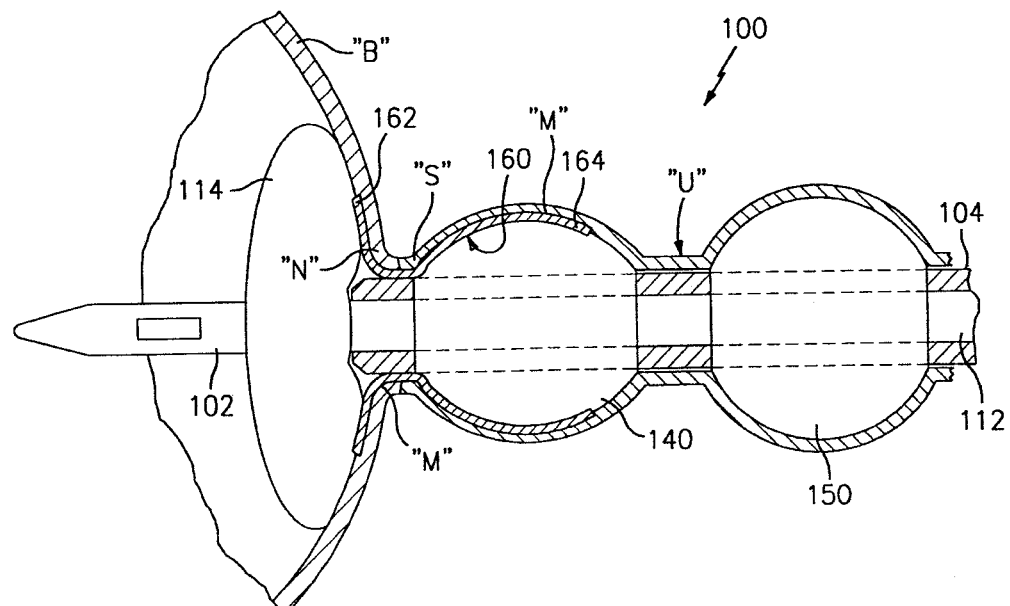
FIG. 7 is a partial cross-sectional side elevational view of a portion of the urinary system illustrating the bladder approximated to the urethra and a device in accordance with the embodiment of FIGS. 1-6 in an anastomosing condition therewithin.

The securement device is desirably deployed so as to maintain the bladder and urethra in the approximated position. In the embodiment shown, withdrawal of inner tubular member 102 through outer tubular member 104 also results in proximal end 164 of sleeve 160 sliding over and being disposed at least partially over distal expandable cuff 140. A fluid (e.g., air, carbon dioxide, saline or the like) is introduced through inflation/deflation lumen 142 (FIG. 8) into distal expandable cuff 140 to thereby expand and inflate distal expandable cuff 140 (see FIG. 6). As seen in FIG. 7, inflation and expansion of distal expandable cuff 140 results in the radial expansion of distal expandable cuff 140 and in turn results in the pressing of distal expandable cuff 140 against the inner surface of proximal end 164 of sleeve 160 which in turn presses against the inner surface of urethra "U". As proximal end 164 of sleeve 160 is expanded radially, sleeve 160 desirably shortens axially which causes bladder neck "N" and urethral stump "S" to become further approximated toward one another and to further ensure sufficient contact exists between bladder neck "N" and urethral stump "S". Other means of securing the position of the body vessels may be used. For example, mechanical interengaging parts on the anchors may be used. The anchors may be left in the body vessels or removed. If left in the body vessels, the anchors desirably comprise bio-absorbable materials and are detachable from the outer and inner tubular members.

Figure 9:
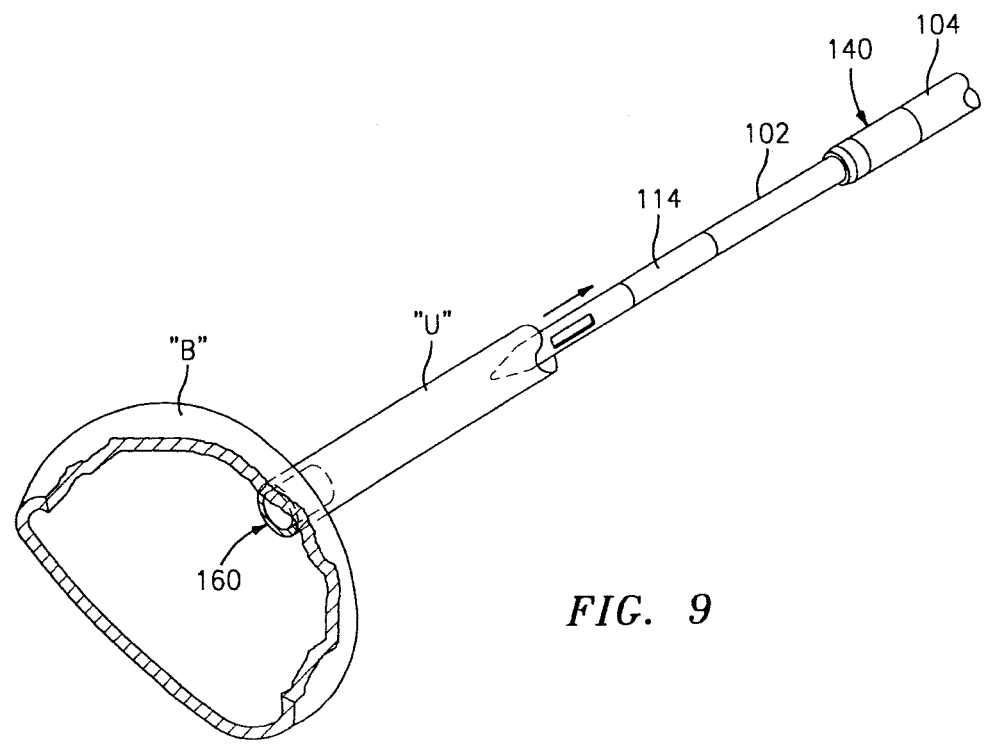
FIG. 9 is an enlarged perspective view of a portion of the urinary system illustrating the withdrawal of a device in accordance with the embodiment of FIGS. 1-8, from the anastomosed bladder and urethra while the device is in the withdrawal condition.

In accordance with the present disclosure, biocompatible medical glue or adhesive "M" can be deployed either through device 100 to the outer surface of sleeve 160 or by a separate surgical instrument or syringe 200 (FIG. 5). Expandable anchor 114 and distal expandable cuff 140 are maintained inflated or expanded until medical adhesive "M" has been given sufficient time to take an initial set (typically several minutes). As seen in FIG. 9, expandable anchor 114, distal expandable cuff 140 and proximal expandable cuff 150 are then deflated or retracted and inner tubular member 102 and outer tubular member 104 are withdrawn from bladder "B" and urethra "U", thus completing the anastomosis. If necessary, the connection between the bladder and urethra may be further secured using other fastening devices, such as staples, clips, sutures, etc. However, it is contemplated that the sleeve 160 is designed and configured for sufficient securement.

Biocompatible adhesive "M" is preferably a non-toxic adhesive having the capability to adhere to biological tissue, reach stability quickly (e.g., typically within about 30 seconds to about 5 minutes), preferably able to set in wet conditions, able to bond to both biological tissues and synthetic materials, and provide sufficient strength. Biocompatible adhesives made up of proteinaceous materials and cross-linking agents have these characteristics. Certain examples of biocompatible adhesives containing protein and a cross-linking agent are disclosed in U.S. Pat. No. 5,385,606 to Kowanko, the entire disclosure of which is incorporated herein by reference.

Preferably, sleeve 160 is fabricated from a bio-absorbable material, such as, for example, polyglycolic acid (PGA) and/or polylactic acid (PLA), so that sleeve 160 may be absorbed into the body over time. Sleeve 160 provides an increased surface area for medical adhesive "M" to adhere to and helps to improve the initial strength and patency of the anastomosis. Preferably, inner tubular member 102 and outer tubular member 104 can be coated with a substance which medical adhesive "M" does not have an affinity for thus allowing for inner tubular member 102 and outer tubular member 104 not to stick to sleeve 160 when they are being withdrawn from bladder "B" and urethra "U".

According to another aspect of the present disclosure, sleeve 160 can be impregnated with medical adhesive "M". In this manner, no modifications need to be made to device 100 and no additional instrument is needed to apply medical adhesive "M" to the outer surface of sleeve 160. According to yet another aspect of the present disclosure, sleeve 160 can include medical adhesive "M" encapsulated within pockets formed therein. Preferably, the pockets are configured to tear or rupture in order to dispense medical adhesive "M" between sleeve 160 and bladder "B", bladder neck "N", urethral stump "S" and urethra "U". In use, when expandable anchor 114 and distal expandable cuff 140 are inflated and expanded, expandable anchor 114 and distal expandable cuff 140 compress the pockets of sleeve 160 against bladder, "B", bladder neck "N", urethral stump "S" and urethra "U" causing the pockets to rupture and release medical adhesive "M". Moreover, the pockets are torn open by the radial expansion of sleeve 160 as expandable anchor 114 and distal expandable cuff 140 are inflated and expanded. The pockets of sleeve 160 may include, for example, encapsulating folds which the seal medical adhesive "M" therein until the expansion of sleeve 160 breaks a severable seal formed on the encapsulating fold thereby releasing medical adhesive "M".

While an annular expandable anchor 114 and annular expandable cuffs 140 and 150 have been shown and described, it is within the scope of the present disclosure that anchor 114 and cuffs 140 and 150 can have a number of shapes and configurations, such as, for example, anchor 114 and each cuff 140 and 150 can comprise a plurality of balloons radially disposed, at least partially, around the outer surface of inner and outer tubular members 102, 104.

Figure 10:
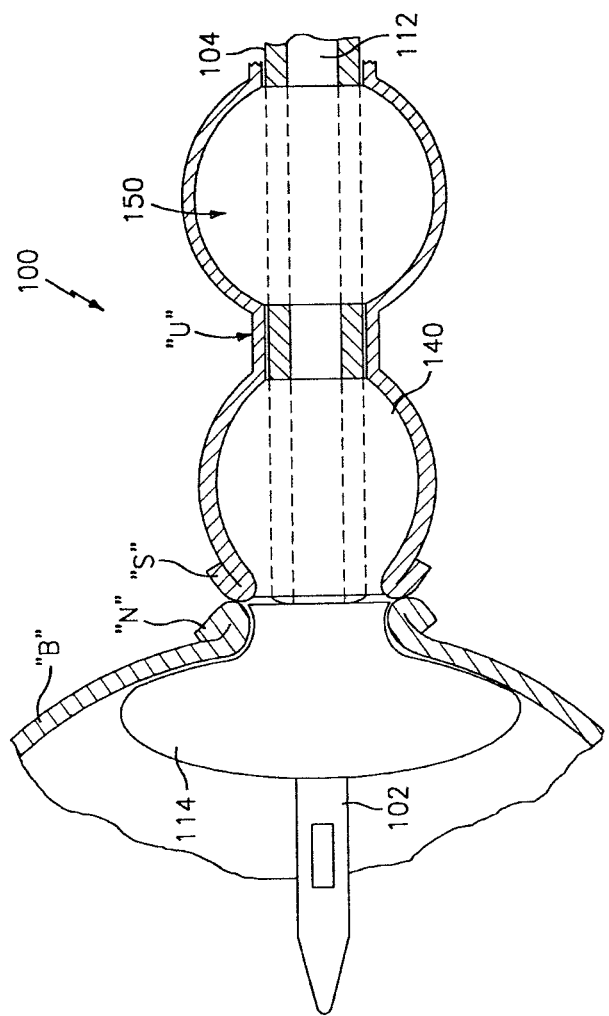
FIG. 10 is a cross-sectional side elevational view of a urinary system illustrating an alternative embodiment of an expandable anchor and an expandable cuff for the device shown in FIGS. 1-9.

Turning now to FIG. 10, an alternative embodiment of a surgical device, substantially similar to device 100 shown in FIGS. 1-9 above, is disclosed with the exception of expandable anchor 114 and expandable cuff 140. As seen in FIG. 10, when in the expanded condition, expandable anchor 114 includes a proximal portion 114a shown in FIG. 10 designed or configured to be concave. Accordingly, in a preferred method of use, proximal portion 114a of anchor 114 is positioned substantially at bladder neck "N" such that when anchor 114 is expanded, proximal portion 114a causes bladder neck "N" to at least partially evert. In addition, as seen in FIG. 10, when in the expanded condition, expandable cuff 140 includes a distal portion 140a, shown in FIG. 10, designed or configured to be concave. Accordingly, in a preferred method of use, distal portion 140a of expandable cuff 140 is positioned substantially at urethral stump "S" such that when expandable cuff 140 is expanded, distal portion 140a causes urethral stump "S" to at least partially evert. In this manner, bladder neck "N" and urethral stump "S" can be everted, to thereby expose the inner mucosal lining to one another, without the need for suturing. Once bladder "B" and urethra "U" are approximated toward one another such that the inner mucosal lining of bladder neck "N" is in contact with the inner mucosal lining of urethral stump "S", biocompatible adhesive "M" or other fastening means is applied circumferentially around the anastomosis to help improve the initial strength and patency of the anastomosis.

It is further envisioned that the proximal end portion of expandable anchor 114 can include a pair of opposed concave surfaces (e.g., a distally oriented concave surface and a proximally oriented concave surface) defining a peak or apex therebetween (not shown). In addition, it is envisioned that expandable cuff 140 includes a distal portion configured and dimensioned to have a diameter substantially equal to the diameter of a proximal end of expandable anchor 114, when both expandable anchor 114 and expandable cuff 140 are in the expanded condition. In a preferred method of use, expandable anchor 114 is positioned within bladder "B" such that bladder neck "N" is positioned distally of the apex. In this manner, as expandable anchor 114 is expanded, the distally oriented concave surface will urge bladder neck "N" to evert. Expandable cuff 140 is then positioned within urethra "U" such that urethral stump "S" preferably extends distally beyond expandable cuff 140. Accordingly, with expandable cuff 140 in the expanded condition, when bladder "B" and urethra "U" are approximated toward one another, the portion of urethral stump "S" extending distally of expandable cuff 140 will preferably cam up or ride up the proximally oriented concave surface of expandable anchor 114. Preferably, urethral stump "S" will ride up and over the everted bladder neck "N" to thereby establish inner mucosal contact with one another. As described above, once bladder "B" and urethra "U" are approximated toward one another biocompatible adhesive "M" or other fastening means is applied circumferentially around the anastomosis to help improve the initial strength and patency of the anastomosis.

While devices in accordance with the present disclosure have been described as being used in connection with radical prostatectomy procedures, it is envisioned that devices having similar structures and modes of operation can be used in various other surgical procedures. Accordingly, it will be understood that various modifications may be made to the embodiments of the presently disclosed devices and methods disclosed herein.

Therefore, the above description should not be construed as limiting, but merely as an exemplification of a preferred embodiment. For example, other expandable anchors may be used. The expandable anchor may comprise a foam or sponge-like material that is expanded upon exposure to moisture, or deployed upon release from a sleeve compressing the anchor. In addition, the device may include one or more expandable balloon-like anchors, in combination with other anchors. Those skilled in the art will envision other modifications within the scope of the present disclosure.

What is claimed is:

1. A method of approximating a first body vessel and a second body vessel, comprising:
    positioning proximal and distal expandable cuffs of an outer tubular member within a distal end of the first body vessel;
    positioning an expandable anchor of an inner tubular member, which is slidably disposed within the outer tubular member, within a proximal end of the second body vessel;
    positioning a sleeve having a distal end portion and a proximal end portion about the outer tubular member such that the distal end portion is disposed at least partially over the expandable anchor;
    expanding the expandable anchor within the second body vessel to press the expandable anchor against an inner surface of the second body vessel to:
        inhibit withdrawal of the inner tubular member from the second body vessel; and
        expand the distal end portion of the sleeve to a diameter greater than the proximal end portion of the sleeve; and
    expanding the proximal expandable cuff within the first body vessel to press the proximal expandable cuff against an inner surface of the first body vessel to prevent axial displacement of the outer tubular member relative to the first body vessel; and
    withdrawing the inner tubular member proximally through the outer tubular member to approximate the proximal end of the second body vessel into contact with the distal end of the first body vessel; wherein the outer tubular member defines a distal end, the distal end of the outer tubular member in contact with the expandable anchor when the expandable anchor is expanded.

2. The method according to claim 1, further comprising locking the inner tubular member in a position relative to the outer tubular member to maintain the approximated position of the first and second body vessels.

3. The method of claim 1, wherein the proximal end portion of the sleeve extends proximally from the second body vessel, and wherein expanding the expandable anchor includes radially expanding the distal end portion of the sleeve within the second body vessel.

4. The method of claim 3, wherein withdrawing the inner tubular member includes sliding the proximal end portion of the sleeve at least partially over the distal expandable cuff.

5. The method of claim 4, further comprising expanding the distal expandable cuff within the first body vessel to radially expand the proximal end portion of the sleeve against the inner surface of the first body vessel.

6. The method of claim 5, wherein the sleeve is fabricated from a material that results in axial shortening upon radial expansion such that during expanding the distal expandable cuff, the first and second body vessels are further approximated into contact with one another.

7. The method according to claim 1, wherein the first body vessel is a urethra and the second body vessel is a bladder.

8. A method of approximating a first body vessel and a second body vessel, comprising:
    inserting a device through a first body vessel and into a second body vessel that is spaced from the first body vessel, the device including:
        an outer tubular member having a proximal expandable cuff and a distal expandable cuff;
        an inner tubular member slidably disposed within the outer tubular member and having a distal end including an expandable anchor; and
        a sleeve made from a material that results in axial shortening upon radial expansion, the sleeve slidably disposed about the outer tubular member and extending at least partially over the expandable anchor and at least partially over the distal expandable cuff,
    such that the proximal and distal expandable cuffs are positioned within the first body vessel and the expandable anchor is positioned within the second body vessel;
    expanding the expandable anchor within the second body vessel to inhibit withdrawal of the inner tubular member from the second body vessel and to radially expand a distal end portion of the sleeve to a first diameter and into contact with the second body vessel; and
    expanding the distal expandable cuff within the first body vessel to radially expand a proximal end portion of the sleeve to a second diameter a into contact with the first body vessel and to axially shorten the sleeve causing the first and second body vessels to approximate towards one another; wherein the outer tubular member defines a distal end, the distal end of the outer tubular member in contact with the expandable anchor when the expandable anchor is expanded.

9. The method according to claim 8, wherein expanding the expandable anchor further includes introducing a fluid through a lumen of the inner tubular member to inflate the expandable anchor.

10. The method according to claim 8, wherein expanding the distal expandable cuff includes introducing a fluid through an inflation/deflation lumen of the outer tubular member to inflate the distal expandable cuff.

11. The method according to claim 8, further comprising expanding the proximal expandable cuff against an inner surface of the first body vessel to prevent axial displacement of the outer tubular member relative to the first body vessel.

12. The method according to claim 11, wherein expanding the proximal expandable cuff includes introducing a fluid through an inflation/deflation lumen of the outer tubular member to inflate the proximal expandable cuff.

13. The method according to claim 8, further comprising withdrawing the inner tubular member proximally through the outer tubular member after expanding the expandable anchor to approximate the second body vessel toward the first body vessel.

14. The method according to claim 8, further comprising locking the inner tubular member in a position relative to the outer tubular member to maintain the approximated position of the first and second body vessels.

15. The method according to claim 8, wherein the distal expandable cuff is positioned within a distal end of the first body vessel such that upon expansion of the distal expandable cuff the distal end of the first body vessel is approximated towards a proximal end of the second body vessel.

16. The method according to claim 8, wherein the first body vessel is a urethra and the second body vessel is a bladder.

\* \* \* \* \*